(12) United States Patent
Wright

(10) Patent No.: US 6,986,353 B2
(45) Date of Patent: Jan. 17, 2006

(54) DIVIDED NASAL CANNULA ASSEMBLY

(75) Inventor: Clifford A. Wright, San Diego, CA (US)

(73) Assignee: Medical Device Group, Inc., Poway, CA (US)

(*) Notice: Subject to any disclaimer, the term of this patent is extended or adjusted under 35 U.S.C. 154(b) by 0 days.

(21) Appl. No.: 10/751,128

(22) Filed: Jan. 3, 2004

(65) Prior Publication Data

US 2004/0139973 A1 Jul. 22, 2004

Related U.S. Application Data

(63) Continuation-in-part of application No. 10/634,365, filed on Aug. 5, 2003, which is a continuation-in-part of application No. 10/224,849, filed on Aug. 21, 2002, now Pat. No. 6,807,966.

(51) Int. Cl.
*A61M 15/08* (2006.01)

(52) U.S. Cl. .............................. 128/207.18; 128/200.26
(58) Field of Classification Search ............ 128/207.18, 128/203.22, 200.26, 202.27, DIG. 26, 204.12, 128/203.18
See application file for complete search history.

(56) References Cited

U.S. PATENT DOCUMENTS

| | | | |
|---|---|---|---|
| 2,168,705 A | * | 8/1939 | Francisco et al. ...... 128/207.18 |
| 2,502,734 A | | 4/1950 | Lyons |
| 2,763,263 A | | 9/1956 | Ellman |
| 2,868,199 A | | 1/1959 | Hudson |
| 3,209,755 A | | 10/1965 | McCarthy et al. |
| 3,682,171 A | | 8/1972 | Dali et al. |
| 3,802,431 A | | 4/1974 | Farr |
| 4,106,505 A | | 8/1978 | Salter et al. |
| 4,156,426 A | | 5/1979 | Gold |
| 4,406,283 A | | 9/1983 | Bir |
| 4,422,456 A | | 12/1983 | Tiep |
| 4,465,065 A | | 8/1984 | Gotfried |
| 4,465,067 A | * | 8/1984 | Koch et al. ............. 128/207.18 |
| 4,535,767 A | * | 8/1985 | Tiep et al. ............. 128/207.18 |
| 4,559,941 A | * | 12/1985 | Timmons et al. ...... 128/207.18 |
| 4,602,644 A | | 7/1986 | DiBenedetto et al. |
| 4,699,139 A | * | 10/1987 | Marshall et al. ....... 128/207.18 |
| 4,708,446 A | * | 11/1987 | Timmons et al. ........... 351/158 |
| 4,739,757 A | | 4/1988 | Edwards |
| 4,753,233 A | | 6/1988 | Grimes |
| 4,808,160 A | | 2/1989 | Timmons et al. |
| 4,836,200 A | | 6/1989 | Clark |
| 4,878,491 A | | 11/1989 | McGilvray, III |
| 5,025,805 A | * | 6/1991 | Nutter .................... 128/207.18 |
| 5,105,807 A | * | 4/1992 | Kahn et al. ............ 128/207.18 |
| 5,117,818 A | * | 6/1992 | Palfy ..................... 128/204.11 |
| 5,137,017 A | * | 8/1992 | Salter .................... 128/207.18 |
| 5,185,005 A | | 2/1993 | Ballantyne |
| 5,193,534 A | * | 3/1993 | Peppler .................. 128/207.1 |

(Continued)

OTHER PUBLICATIONS

U.S. Appl. No. 60/341,923, filed Dec. 19, 2001, Gupta.

*Primary Examiner*—Henry Bennett
*Assistant Examiner*—Mital Patel
(74) *Attorney, Agent, or Firm*—Fish & Richardson P.C.; Mikael Havluciyan; Fred C. Hernandez

(57) ABSTRACT

A nasal cannula system includes a nasal cannula for the delivery of and collection of gases, wherein the nasal cannula is coupled to a pair of extension tubes which are slidingly received within right and left earpieces respectively for retaining and securing the extension tubes to fix the cannula in a desired position for use by a patient. Each nasal cannula includes an open recessed channel disposed between a pair of bridges for retaining the extension tube within the earpiece and an locking exit hole at its distal end for helping to secure therein the extension tube to provide a fixed distance adjustment between the nasal cannula and the ears of the patient.

20 Claims, 10 Drawing Sheets

U.S. PATENT DOCUMENTS

| | | | |
|---|---|---|---|
| 5,271,391 A | | 12/1993 | Graves |
| 5,308,337 A | * | 5/1994 | Bingisser .................... 604/174 |
| 5,400,776 A | * | 3/1995 | Bartholomew ......... 128/200.24 |
| 5,438,979 A | * | 8/1995 | Johnson et al. ........ 128/207.18 |
| 5,636,630 A | | 6/1997 | Miller et al. |
| 5,682,881 A | * | 11/1997 | Winthrop et al. ...... 128/207.18 |
| 6,298,850 B1 | | 10/2001 | Argraves |
| 6,328,038 B1 | | 12/2001 | Kessler et al. |
| 6,439,234 B1 | | 8/2002 | Curti et al. |
| 6,505,624 B1 | * | 1/2003 | Campbell, Sr. ........ 128/207.18 |
| 6,561,193 B1 | * | 5/2003 | Noble .................... 128/207.18 |
| 6,655,385 B1 | | 12/2003 | Curti et al. |
| 6,679,265 B2 | | 1/2004 | Strickland et al. |
| 6,684,883 B1 | * | 2/2004 | Burns .................... 128/207.18 |
| 6,807,966 B2 | | 10/2004 | Wright |
| 2002/0112730 A1 | | 8/2002 | Dutkiewicz |
| 2003/0111081 A1 | | 6/2003 | Gupta |
| 2003/0189492 A1 | | 10/2003 | Harvie |
| 2004/0035431 A1 | | 2/2004 | Wright |

\* cited by examiner

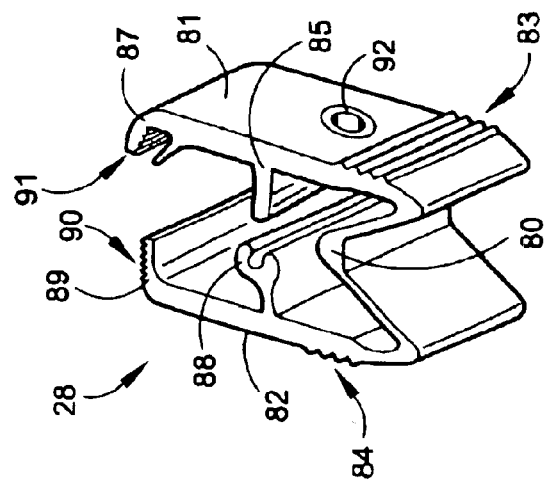
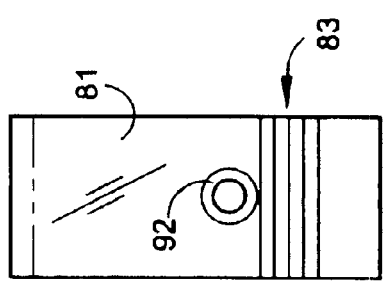
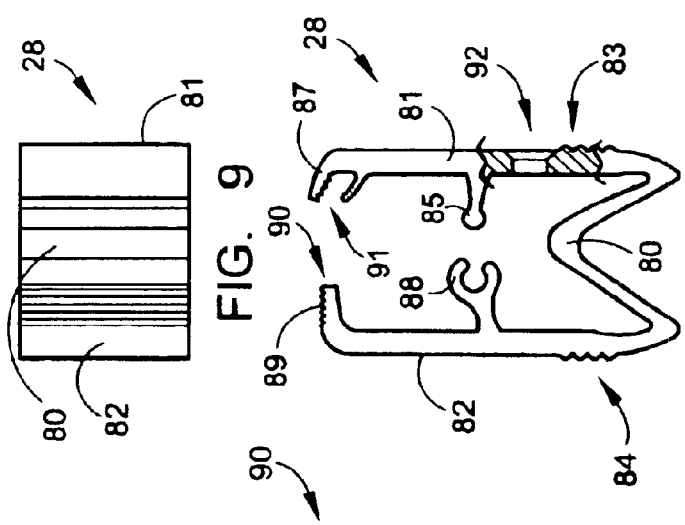
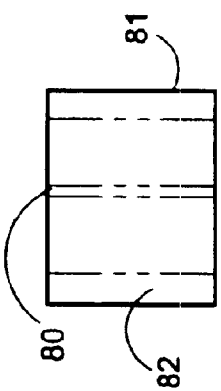
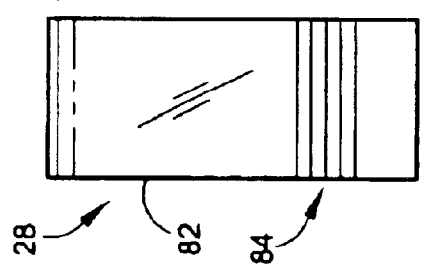

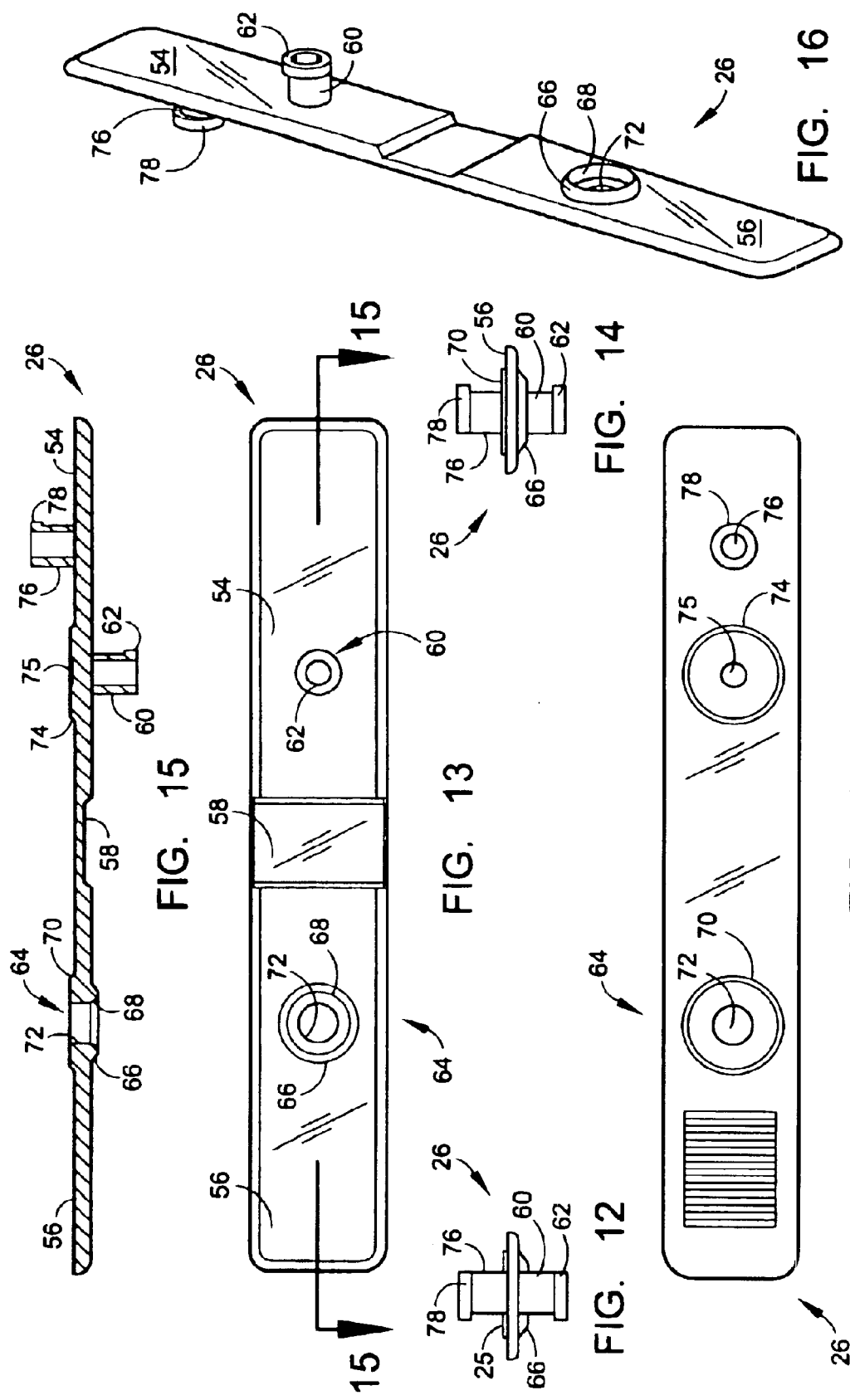

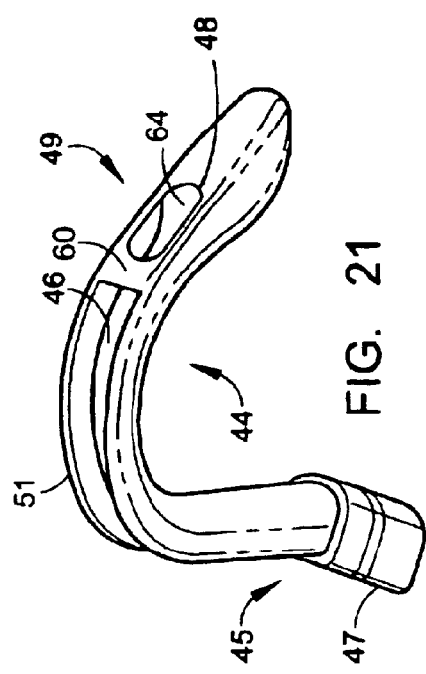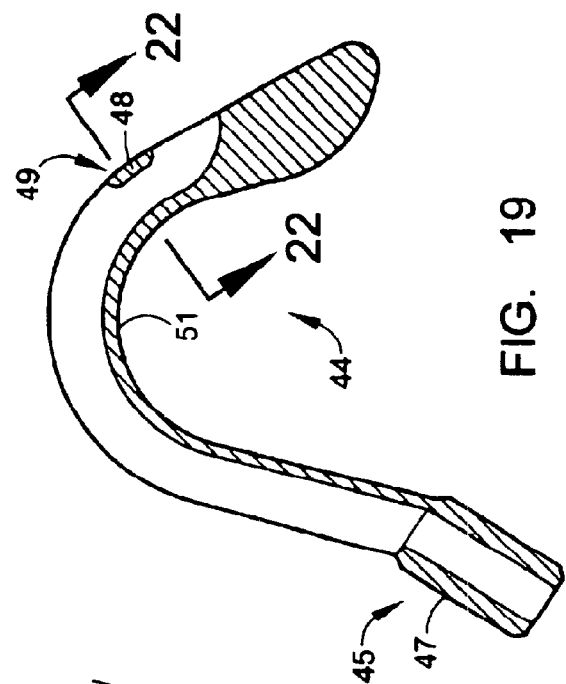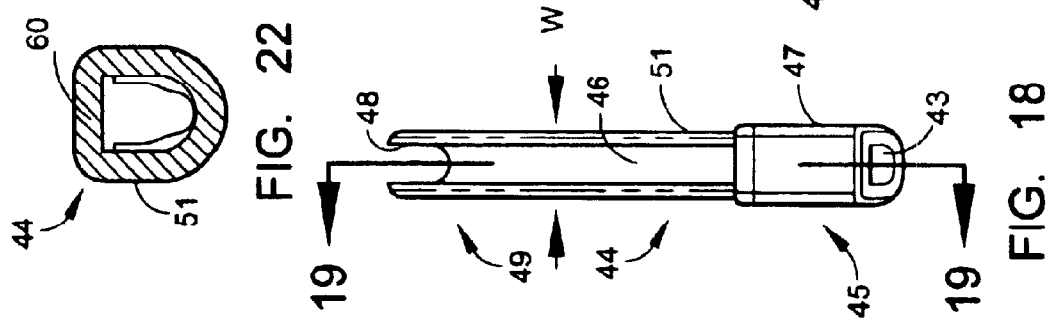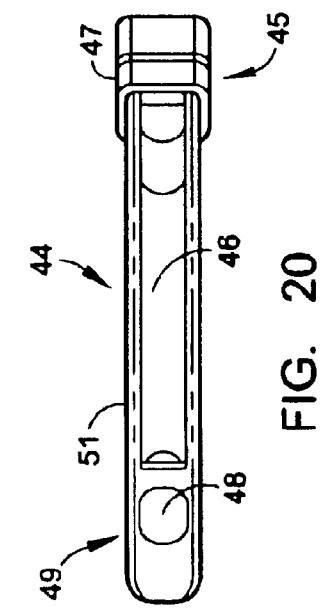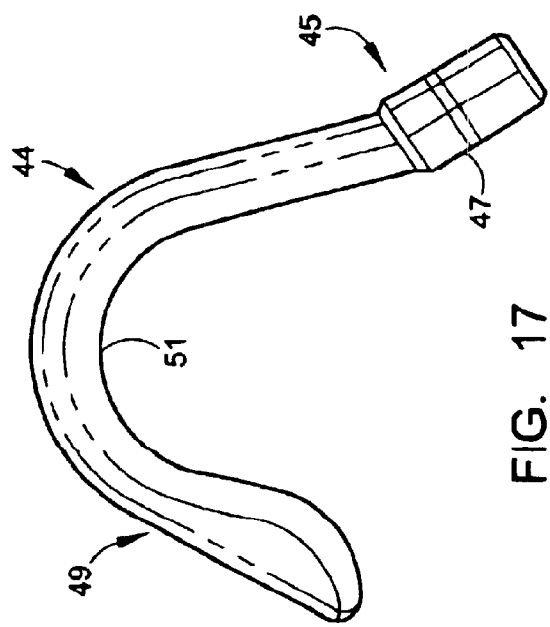

DIVIDED NASAL CANNULA ASSEMBLY

RELATED APPLICATIONS

This is a continuation-in-part of U.S. patent application Ser. No. 10,634,365 Entitled "Ear Cannula System and Method of Using Same", Filed Aug. 5, 2003, now U.S. Pat. No. 20040035431 which is a continuation-in-part of U.S. patent application Ser. No. 10/224,849 Entitled "Oxygen Delivery System and Method of Using Same", filed Aug. 21, 2002, now U.S. Pat. No. 6,807,966.

FIELD OF THE INVENTION

This invention relates in general to oxygen delivery system, and more particularly to an oxygen delivery system that includes a divided nasal cannula assembly having earpieces and extension tubes for securing the nasal cannula at a desired position on a user.

BACKGROUND

Oxygen delivery systems that include nasal cannulas are well known in the art. Examples of such prior art systems include U.S. Pat. Nos.: 6,328,038 B1; 6,298,850; 5,682,881; 5,636,630; 5,438,979; 5,271,391; 5,117,818; 5,025,805; 4,836,200; 4,808,160; 4,753,233; 4,739,757; 4,699,139; 4,422,456; 4,406,283; 4,156,426; 4,106,505; 3,802,431; 2,868,199; 2,763,263; and 2,168,705.

While nasal cannulas are a convenient method of supplying a patient with oxygen enriched gases, it would be highly desirable to have a new and improved oxygen delivery system that includes a nasal cannula that is easily adjusted for the comfort of the patient and that is not prone to falling off the face of the patient.

SUMMARY OF THE INVENTION

A nasal cannula assembly includes a split nasal cannula having a pair of spaced nasal prongs for delivery and sampling of gases respectively, which are inhaled and exhaled by a patient. One side of the nasal cannula is coupled to an gas delivery source through a gas delivery extension tube that passes through a front eye hole, along a curved open recessed extension tube channel and out of a locking eye hole, all forming part of an elongated flexible earpiece that is adapted to be hooked onto a top portion of one ear of the user. The other side of the nasal cannula is coupled to a gas sampling source through a gas sampling extension tube that passes through another front eye hole, along another curved open recessed extension tube channel and out of another locking eye hole, all forming part of another elongated flexible earpiece that is adapted to be hooked onto a top portion of the other ear of the user.

BRIEF DESCRIPTION OF THE DRAWINGS

FIG. 5 is a bottom view of a plastic clip forming part of the ear cannula system of FIG. 1;

FIG. 6 is a left side plane view of the plastic clip forming part of the ear cannula system of FIG. 1;

FIG. 7 is a front plane view of the plastic clip forming part of the ear cannula system of FIG. 1;

FIG. 8 is a right side plane view of the plastic clip forming part of the ear cannula system of FIG. 1;

FIG. 9 is a top plane view of the plastic clip forming part of the ear cannula system of FIG. 1;

FIG. 10 is a pictorial view of the plastic clip forming part of the ear cannula system of FIG. 1;

FIG. 11 is a bottom plane view of a mounting strap forming part of the ear cannula system of FIG. 1;

FIG. 12 is a left side plane view of the mounting strap forming part of the ear cannula system of FIG. 1;

FIG. 13 is a top plane view of the mounting strap forming part of the ear cannula system of FIG. 1;

FIG. 14 is a right side plane view of the mounting strap forming part of the ear cannula system of FIG. 1;

FIG. 15 is a section view of the mounting strap taken along line 15—15 of FIG. 13;

FIG. 16 is a pictorial view of the mounting strap forming part of the ear cannula system of FIG. 1;

FIG. 17 is a front plane view of an earpiece forming part of the ear cannula system of FIG. 1;

FIG. 18 is a side plane view of the earpiece forming part of the ear cannula system of FIG. 1;

FIG. 19 is a section view of the earpiece taken along line 19—19 of FIG. 18;

FIG. 20 is a top plane view of the earpiece forming part of the ear cannula system of FIG. 1;

FIG. 21 is a pictorial view of the earpiece forming part of the ear cannula system of FIG. 1;

FIG. 22 is a cross sectional view taken along line 22—22 of the earpiece of FIG. 19;

DETAILED DESCRIPTION

Figure 1:
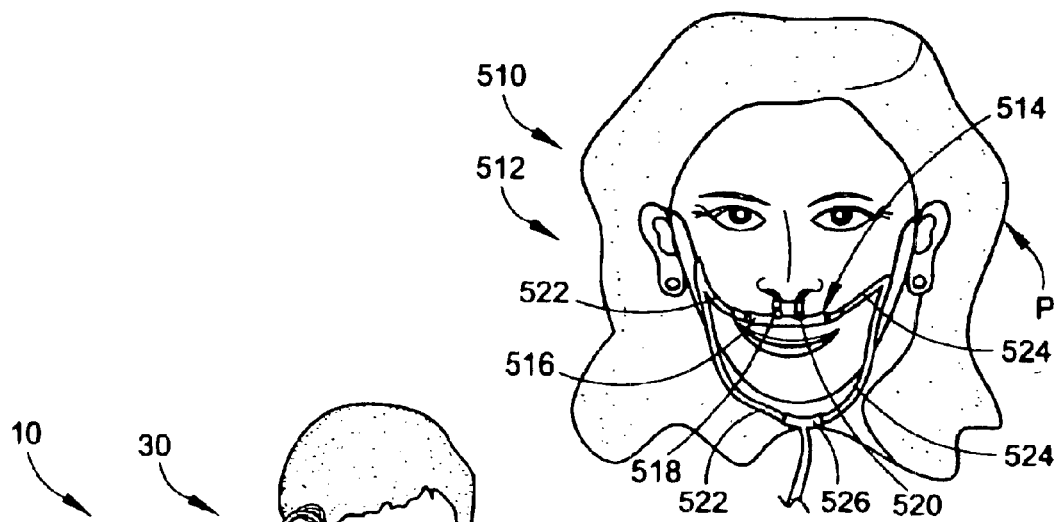
FIG. 1 depicts a frontal view of a patient's head showing a typical prior art nasal cannula arrangement for delivering oxygen to a patient.

Before discussing the preferred embodiment of the present invention, it may be beneficial to briefly review a typical prior art oxygen delivery system 510 that utilizes a nasal cannula 512. In this regard, as best seen in FIG. 1, the nasal cannula 512 generally comprises a nosepiece or nasal assembly 514 having a hollow body member 516 with two upstanding nose prongs or nasal extension tubes 518 and 520 that are adapted to be placed in the nasal cavities of the patient P. Oxygen (from a source not shown) is supplied to the hollow body member 516 at ones of its end openings allowing the body member 516 to functions as a gas distribution manifold. Generally, a pair of gas supply tubes 522 and 524 are attached to the nosepiece 514, that is supported or held in place by extending the gas supply tubes 522 and 524 from the nosepiece 514 to respective ones of the ears of the patent P so the tubes 522 and 524 pass behind respective ones the ears of the patient P. The extension tubes 522 and 524 are bent downward behind the ears and traverse along the jaw area and are then secured together by a cinch 526 or an adjustable loop that is tightened below the chin of the patient to hold the nosepiece in place. The tubes are then joined in by a reducer (not shown) so that a single gas line is available to be attached to the oxygen or air source. From the foregoing, it should be understood that the looping tubes that extend around the ears of the user and along the jaw area of the patient and down to the neck area are uncomfortable and can be dislodged if the cinch 526 is not properly adjusted to tighten the loops sufficiently around the ears of the patient P in a somewhat uncomfortable manner.

Therefore the is a need for a new and improved oxygen delivery system that includes a nasal cannula that is easily adjusted for the comfort of the patient and that is not prone to falling off the face of the patient.

Figure 2:
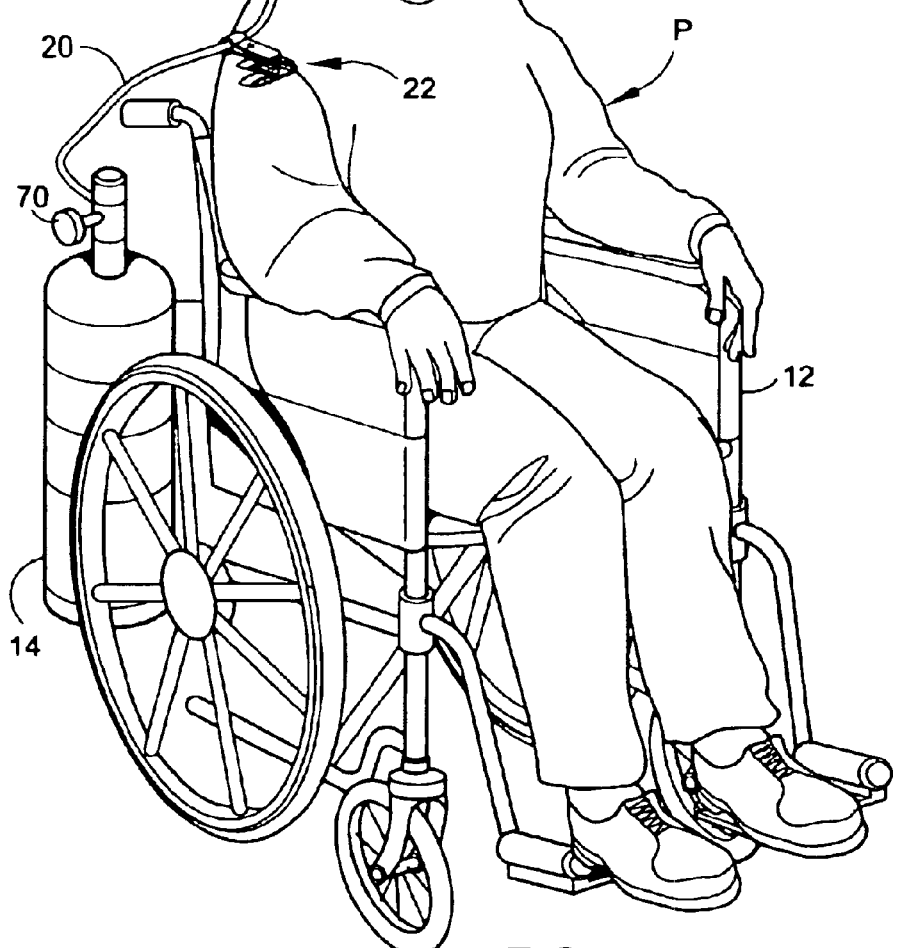
FIG. 2 depicts a perspective view of a patient using a preferred embodiment of the present invention.
Figure 3:
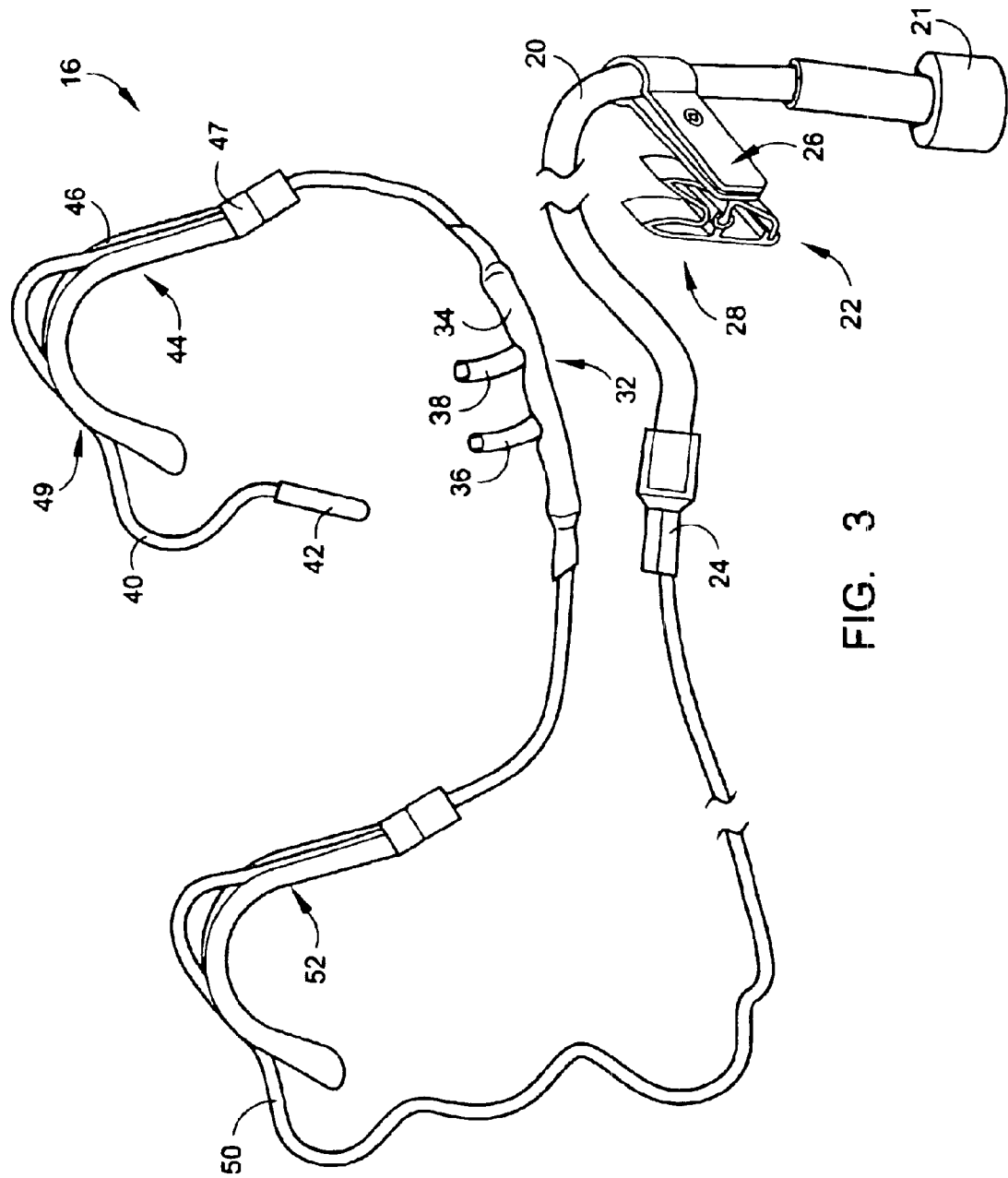
FIG. 3 depicts an ear cannula system, which is constructed in accordance with the present invention.

Referring now to the drawings and more particularly to FIGS. 2–3, there is shown a cannula system 10 that is constructed in accordance with the present invention. The cannula system 10 is illustrated being utilized by a patient P who is sitting in a wheelchair 12 that is adapted to transport a source of oxygen or air shown generally at 14.

Considering now the cannula system 10 in greater detail, the cannula system 10, generally comprises a nasal cannula assembly 16 and a flexible tube member 20 that cooperate to facilitate the delivery of air to the lung of the patient P. The flexible tube member 20 is held within a securing arrangement 22 that permits the tube member 20 to be secured to the shirt of the patient P or to a bottom bed sheet of a bed should the patient be confined to a bed.

In order to provide the nasal cannula assembly 16 with a supply of air, the flexible tube member 20 is connected at ones of its ends to a universal connector 21 that permits the flexible tube member 20 to be attached to the source of oxygen 14. A reduction connector 24 is connected to the other end of the flexible tube member 20 that permits the flexible tube member 20 to be attached to the nasal cannula assembly 16. As will be explained hereinafter in greater detail, the nasal cannula assembly 16 is adapted to be comfortably supported from the ears of the patient P.

Considering now the nasal cannula assembly 16 in greater detail with reference to FIG. 3, the nasal cannula assembly 16 generally includes a nasal delivery tube or cannula nosepiece 32, a pair of adjustment or extension tubes 40 and 50 respectively, and a pair of ear pieces 44 and 52 respectively. The extension tubes 40 and 50 are slidably mounted to the ear pieces 44 and 52 respectively in such a manner to facilitate supporting the cannula nosepiece 32 from the ear pieces 44 and 52 and to help facilitate adjusting the distance between the nosepiece 32 and individual ones of the ear pieces 44 and 52 so the cannula nosepiece 32 can be properly position relative to the nostrils of the patient P.

Considering the nasal cannula assembly 16 in still greater detail, the cannula nosepiece 32 includes a hollow body member 34 with two upstanding nose prongs or nasal extension tubes 36 and 38. The nose prongs 34 and 36 are adapted to be placed in the nasal cavities of the patient P as best seen in FIG. 2. In this manner, when the cannula nosepiece 32 is supported in the nasal cavities of the patient P it facilitates the delivery of oxygen to the lungs of the patient P in a comfortable and convenient manner. The nose prongs 34 and 36 are spaced apart from one another and have a sufficient length so as not to be dislodged from the nostrils of the patient. In this regard, the nose prongs 34 and 36 may be adjusted by cutting or trimming their ends with a pair of scissors (not shown) to a proper length to be comfortable to an individual patient, such as the patient P.

The hollow body member 34 is connected at its distal end in an airtight manner to the extension tube 40, which is plugged at its distal end with a plastic stop 42. The extension tube 40 is supported spaced from the ear of the patient P by the earpiece 44. As best seen in FIG. 18, the earpiece 44 has a recessed channel 46 and a pair of locking eyeholes or tube guides 47 and 48 respectively. In this regard, the extension tube 40 is sufficiently long to pass by its distal end through the front tube guide 47 and then along the channel 46 exiting at a rear portion 49 of the earpiece 44 through the rear tube guide 48. The channel 46 is sufficiently narrow to hold or capture the extension tube 40 against the earpiece 44, but not so narrows as to prevent the extension tube 40 from being pulled under a directed force through the channel 46 to a desired position.

As best seen in FIGS. 21–22, the rear portion 49 includes a bridge 60 having an exit hole 48 that has a shape that is similar to hole 43. The tube guide 47 and the bridge 60 cooperate to capture the extension tube respectively at its entrance and exit points to the channel 46. This assures the extension tube 40 cannot be grasped and pulled out of the earpiece. This is an important feature of the present invention as it helps to assure that the cannula will remain secured to the earpiece via the extension tube 40, which can only be removed by pulling the extension tube 40 in a direction toward the cannula and out of the earpiece via the tube guide hole 43.

As best seen in FIG. 21, the recessed channel 46 terminates at the hole 48. In this regard, the channel 46 rises upward through the hole 48 to form a ramp 64 with about a forty-five degree upward slant. This is an important feature of the present invention as the ramp 64 is structured to cause the extension tube 40 to be pressed against the flat top surface of the exit hole 48 with sufficient force to wedge the tube 40 against this surface. In this regard, the wedging force is sufficient to retain or secure the extension tube 40 between the two holes, the exit hole 48 and tube guide hole 43 but not such a sufficient force as to prevent the extension tube 40 from being pulled back and forth through the two holes for distance adjustment purposes. In this manner the patient P or a health care provider (not shown) may adjusts the distance between the nasal cannula 32 and the ear piece 44 to help position the nasal cannula 32 in proper position relative to the nostrils of the patient P for delivery of fluids to the lungs of the patient P.

From the foregoing those skilled in the art will understand that the stop 42 is attached to the distal end of the extension tube 40 after the tube 40 has been attached to the earpiece 44. Those skilled in the art will further understand that extension tube 40 is supported from the ear piece 44 in such a manner that the tube 40 does not rub against and irritate the ear of the patient P and that the extension tube 40 and ear piece 44 cooperate with one another to support the nosepiece 32 much in the same way as glass lens are supported but without the necessity of utilizing the bridge of the nose since the nosepiece 32 is substantially lighter in weight than that of glasses. This arrangement therefore eliminates the necessity of looping tubes around the ears of the user and along the jaw area and chin area thereby allowing the nosepiece 32 to be worn and supported in a very comfortable manner from the ears of the patient P.

As best seen in FIG. 3, the hollow body member 34 is coupled at its proximate end to the other extension tube 50 whose distal end is coupled in an airtight manner to the reduction connector 24. In this manner, a fluid or air path is established between the oxygen source 14 and the nasal cannula assembly 16 when the extension tube 50 is interconnected to the reduction connector 24. In the preferred embodiment of the present invention, the reduction connector 24 has been described as being attached to the flexible tube member 20. It should be understood however, by those skilled in the art, that the reduction connector 24 could be attached to the end of the extension tube 50 as part of the nasal cannula assembly 16.

The extension tube 50 is slidably mounted to the earpiece 52 and cooperates with the earpiece 52 to further facilitate supporting the cannula nosepiece 32. As the earpiece 52 is similar in construction to the earpiece 44, earpiece 52 will not be described hereinafter in greater detail. In a similar nature, as the manner of adjusting the position of the cannula nosepiece 32 relative to the ear piece 52 is substantially similar as the distance adjustment between the earpiece 44 and the cannula nosepiece 32, no further disclosure relative to adjustment is necessary.

From the foregoing it should be understood, that the nasal cannula assembly 16 is light in weight, is easily attached to an oxygen source, such as the oxygen source 14, utilizing a single tube path, and can be easily adjusted to fit and be supported from the ears of any patient, such as the patient P. Another important feature of the preferred embodiment of the present invention is that the nasal cannula assembly 16 is compact, simple in construction and does not necessitate the utilization of looping tubes around the ears of the user and along the jaw area and chin area thereby allowing the cannula 32 to be worn and support in a very comfortable manner.

Figure 4:
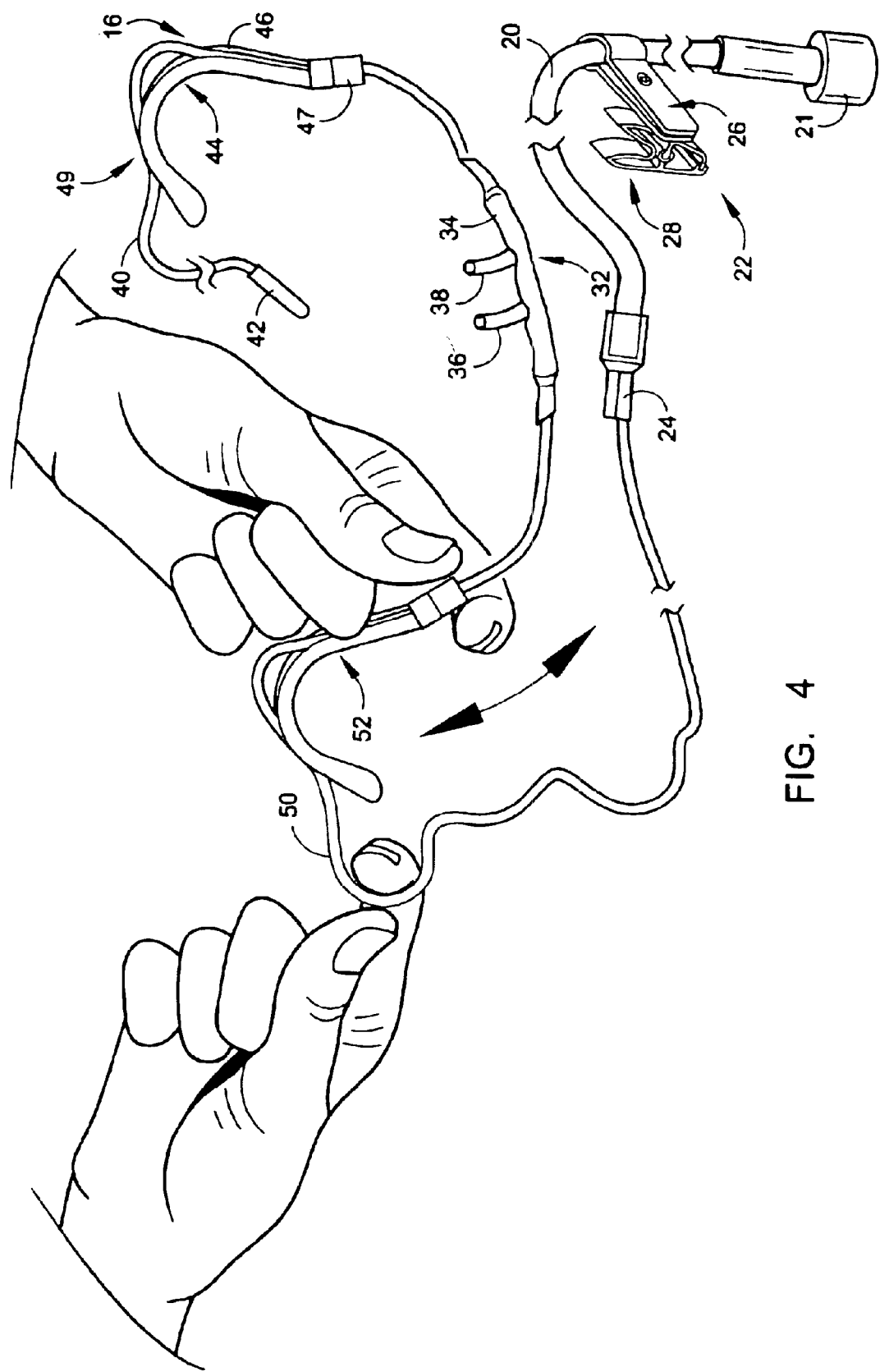
FIG. 4 depicts an adjustment step in the novel method of using the oxygen system.

Considering now the novel method of using the cannula system 10 with reference to FIGS. 2–4, the patient P first inserts the nostril prongs 34 and 36 of the nosepiece 32 into his or her nostrils to make certain that their overall length is a comfortable fit within the nostrils. If not, the tips of the prongs 34 and 36 may be cut to adjust them to a sufficient length to facilitate the comfort of the patient P. Next as best seen in FIG. 2, the patient P hooks the earpieces 44 and 52 around his or her ears in the same manner as if putting on a pair of glasses allowing the nasal cannula nosepiece 32 to be freely supported by the ears of the patient P. If the nose piece 32 is not properly supported within the nostrils of the patient P, the patient P or a healthcare provider may grasps the extension tube 40 between his or her thumb and forefinger at about its exit point from the rear guide 48 of the ear piece 44 and the earpiece 44 between the thumb and forefinger of his or her other hand and then gently pull the extension tube 40 rearward to cause the cannula nosepiece 32 to move closer to the ear piece 44. Conversely, if the cannula nosepiece 32 needs to be adjusted so that it is moved further away from the earpiece 44, the patient may grasps the extension tube 40 between his or her thumb and forefinger at about its entry point into the front guide 47 and the ear piece 44 between the thumb and forefinger of his or her other hand and then gently pull the tube 40 forward to move the cannula nosepiece 32 further away from the earpiece 44. This procedure is repeated until the cannula nosepiece 32 is positioned at a proper distance from earpiece 44. Once the nasal cannula has been adjusted to a proper position, any excess of the extension tube 40 that is disposed above the lip 51 of the recessed channel 46 is pull down into the channel 46 by the patient grasping the tube exiting through hole 48 and pulling it gently rearward until the excess extension tube 40 is completely disposed within the channel 46. In this regard, the extension tube 40 is locked at about the exit hole 48 because it is wedged between the bridge 60 and the bottom of the ramp 64.

Next as best seen in FIG. 4, the above described procedure is repeated by the patient grasping the extension tube 50 between his or her thumb and forefinger at about its exit point from the rear guide of the ear piece 52 and the ear piece 52 between the thumb and forefinger of his or her other hand and then gently pulls the extension tube 50 rearward to move the nosepiece 32 closer to the earpiece 52. Conversely, if the nosepiece 32 needs to be adjusted so that it is moved further from the earpiece 52, the patient P may grasps the extension tube 50 between his or her thumb and forefinger at about its entry point into the front guide and the ear piece 52 between the thumb and forefinger of his or her other hand and then gently pulls the tube 50 forward to move the nosepiece 32 further away from the earpiece 52. This procedure is repeated until the nosepiece 32 is positioned at a proper distance from ea piece 52, thereby allowing the nose prongs 36 and 38 to be pulled up into the nostrils of the patient where they are disposed in a comfortable position and supported by the ear pieces 44 and 52 supported from the ears of the patient P.

In a final step, the patient couples the distal end of the extension tube 50 to the flexible tube 20, which was previously coupled to the source of air 14 as best seen in FIG. 2. The patient P may then turn on the supply of air using an actuation knob 70 allowing the free flow of oxygen to the nosepiece 32 for distribution into the lungs of the patient P.

Considering now the securing arrangement 22 in greater detail with reference to FIGS. 3–16, the securing arrangement 22 generally includes a flexible plastic strap 26 and a plastic clip 28. The flexible strap 26 is adapted to be secured in a friction tight fit around the tube member 20 without pinching or closing off the flow of fluids within the tube member 20, and is further adapted to be coupled to the plastic clip 28 for holding the clip 28 in a stationary position relative to the strap 26. From the foregoing it should be understood by those skilled in the art that the securing arrangement 22 is composed on two plastic parts that are coupled together without the use of any metallic parts, which allows the arrangement 22 to be easily and quickly assembled at a relatively low cost.

Considering now the flexible plastic strap 26 in greater detail with reference to FIGS. 11–16, the strap 26 is generally rectangular in shape having right side portion 54 and a left side portion 56 which are separated from one another by centrally disposed cutout section 58. The right side portion 54 and the left side portion have an overall thickness that is substantially greater the thickness of the cutout section 58. In this regard, the thickness of the cutout section 58 is sufficient thin to allow the plastic to wrap around the tube member 20 as best seen in FIGS. 3–4, without pinching the tube 20 so that it is incapable of a sustained flow of fluid under pressure from the air source 14.

In order to facilitate securing the strap 26 around the tube 20, the right side portion 54 includes an upstanding post 60 having a flange at its distal end. The flange 62 is slightly offset from the post 60 and is constructed to be received within a catch 64 that extends through the left side portion 56. More particularly, the catch 64 has a slight boss 66 with a tapered opening 68 on its one side in the same plane as the post 60 and another slight boss 70 with a cylindrical opening 72 on its side opposite to the post 60. With this construction, the flange 62 slides within the tapered opening 68 and passes through the opening 72 allowing the post 60 to snap into locking engagement within the boss 70. As best seen in FIG. 12, the post 60 extends a significant distance beyond the upper surface of the boss 70. This is an important feature, as post 60 acts as an anchor point for the clip 28 as will be explained hereinafter in greater detail.

As best seen in FIGS. 11 and 15, the right side portion of the strap 26 includes another slight boss 74 having a centrally disposed opening 75 that is disposed opposite the post 60. The boss 74 functions as a finger receiving area for facilitating pressing post 60 into hole 72 when the strap 26 is attached to tube 20 as best seen in FIGS. 3–4. The right side portion 54 of the strap 26 also includes another post 76 that is disposed slightly outward from the boss 74. The post 76 includes a flange 78 at its distal end that is slightly offset from the post 76 to facilitate capturing the post 76 in hole 92 of the clip 83 as best seen in FIG. 10.

Considering now the plastic clip 28 in greater detail with reference to FIGS. 5–10, the plastic clip 28 includes a V-shaped pincher 80 that is centrally disposed and integrally connected between a right leg member 81 and a left leg member 82. The outer surface area of the right leg member 81 and the left leg member 82 each include a plurality of finely spaced apart finger engagable ridges indicated generally at 83 and 84 respectively. The ridges 83, 84 help keep the finger surfaces of the patient engaged with the upper surfaces of the leg members 81, 82 when the leg members 81, 82 are pinched toward one another at about the pincher 80.

As best seen in FIG. 7, the right leg member 81 includes a centrally disposed male member 85 which extends inward toward the center of clip 28 and a female member 87 which is disposed at the distal end of the right leg member 81 farthest from the pincher 80. The left leg member 82 includes a centrally disposed female member 88 which extends inward toward the center of the clip 28 and a male member 89 which is disposed at the distal end of the left leg member 82 farthest from the pincher 80. The male member 85 and the female member 88 are aligned so that when the right leg member 81 and the left leg member 82 are pinched toward one another the male member 85 and the female member 88 will come into locking engagement with one another. In a similar manner, the female member 87 and the male member 89 are aligned so that when the right leg member 81 and the left leg member 82 are pinched toward one another the female member 87 receives the male member 89.

In order to help facilitate the capture of a cloth material between the female member 87 and the male member 89 each of the members 87 and 89 include a plurality of ridges and valleys indicated generally at 90 and 91 respectively.

As best seen in FIGS. 7–8, the right leg member 81 of the clip 26 includes a tapered wall opening 92 that is dimensioned for receiving in locking engagement the post 60. In this regard, the flange 62 and post have a sufficient length to pass through the opening 92 and to be captured against the inner wall of the right leg member 81.

Considering now the earpiece 44 in greater detail with reference to FIGS. 17–21, the earpiece 44 and earpiece 52 are identical to one another and both are composed of a soft elastomeric material that is common to glassware earpieces. The earpiece 44 is a molded and includes a front part 45, which includes the front tube guide 47 having a generally U-shaped hole 43 extending therethrough, a central hook portion, which includes a sharply curved rear channel section 46 that terminates in a lip 51 and a rear part 49 that includes the ram 64 disposed at about the exit guide hole 48.

Figure 23:
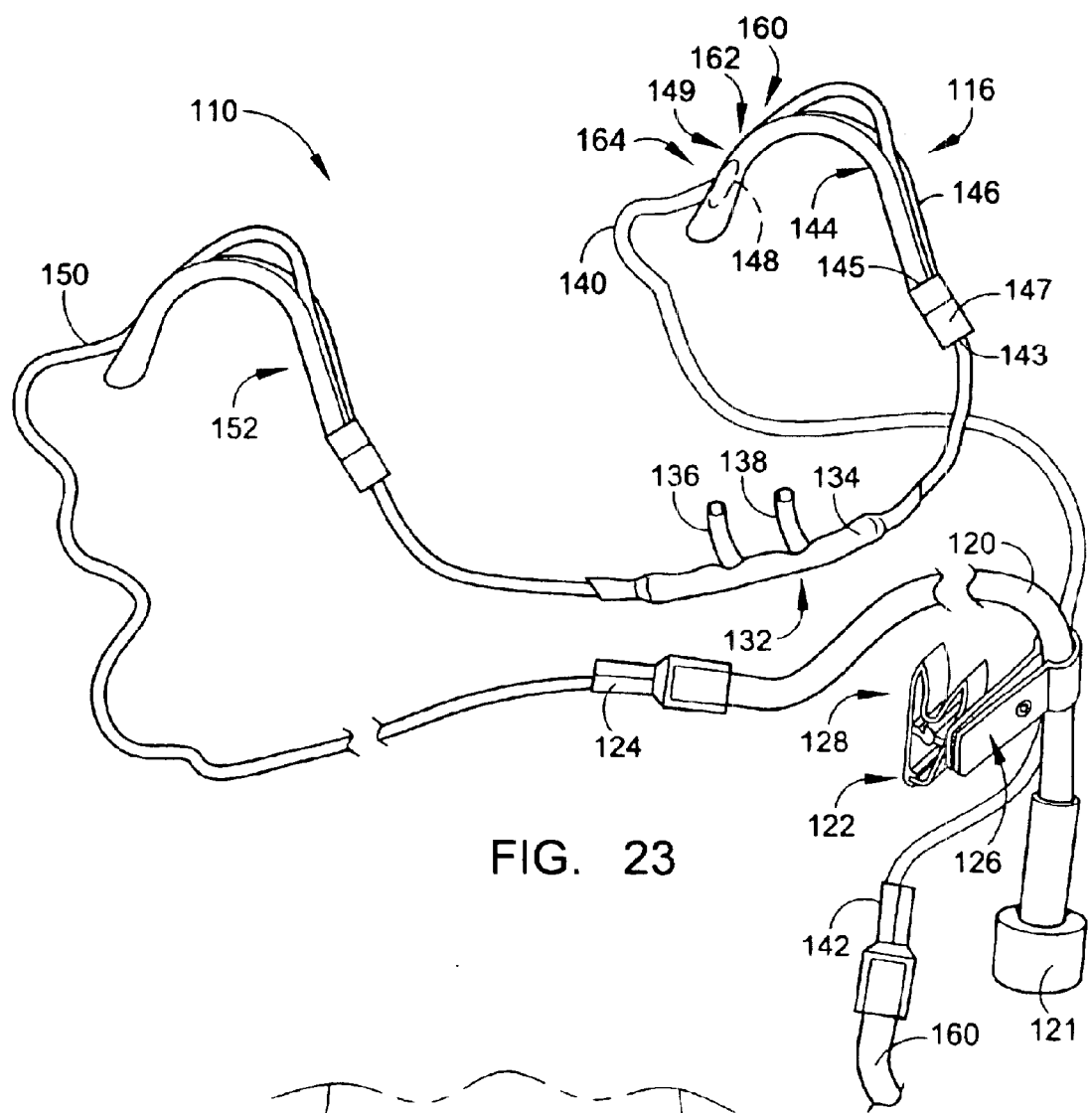
FIG. 23 is a pictorial view of a preferred embodiment of a nasal cannula assembly, which is constructed in accordance with the present invention and which forms part of the nasal cannula system of FIG. 31.
Figure 24:
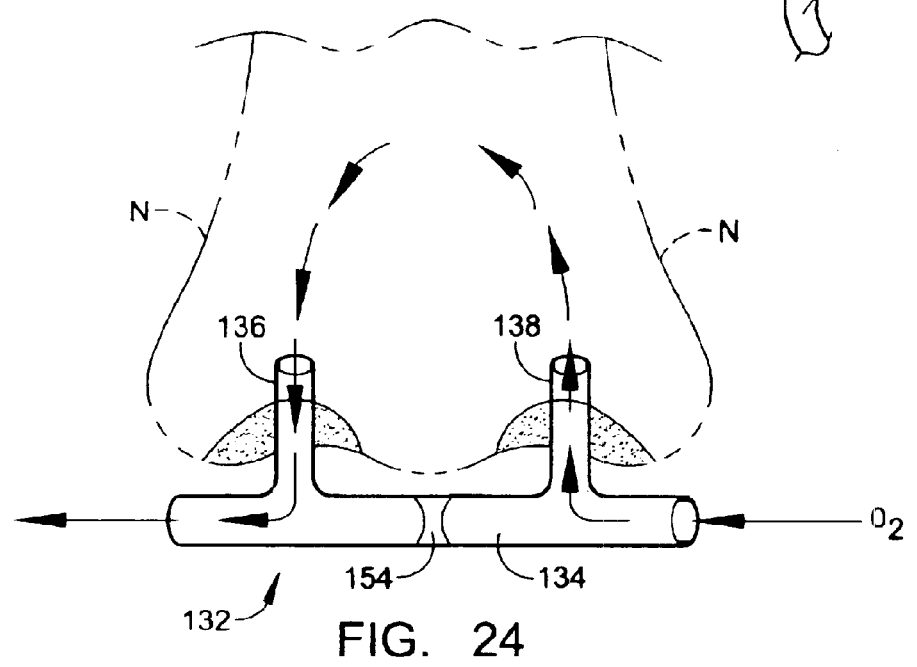
FIG. 24 is a nasal oxygen/carbon dioxide cannula forming part of the nasal/oral cannula assembly of FIG. 24.
Figure 31:
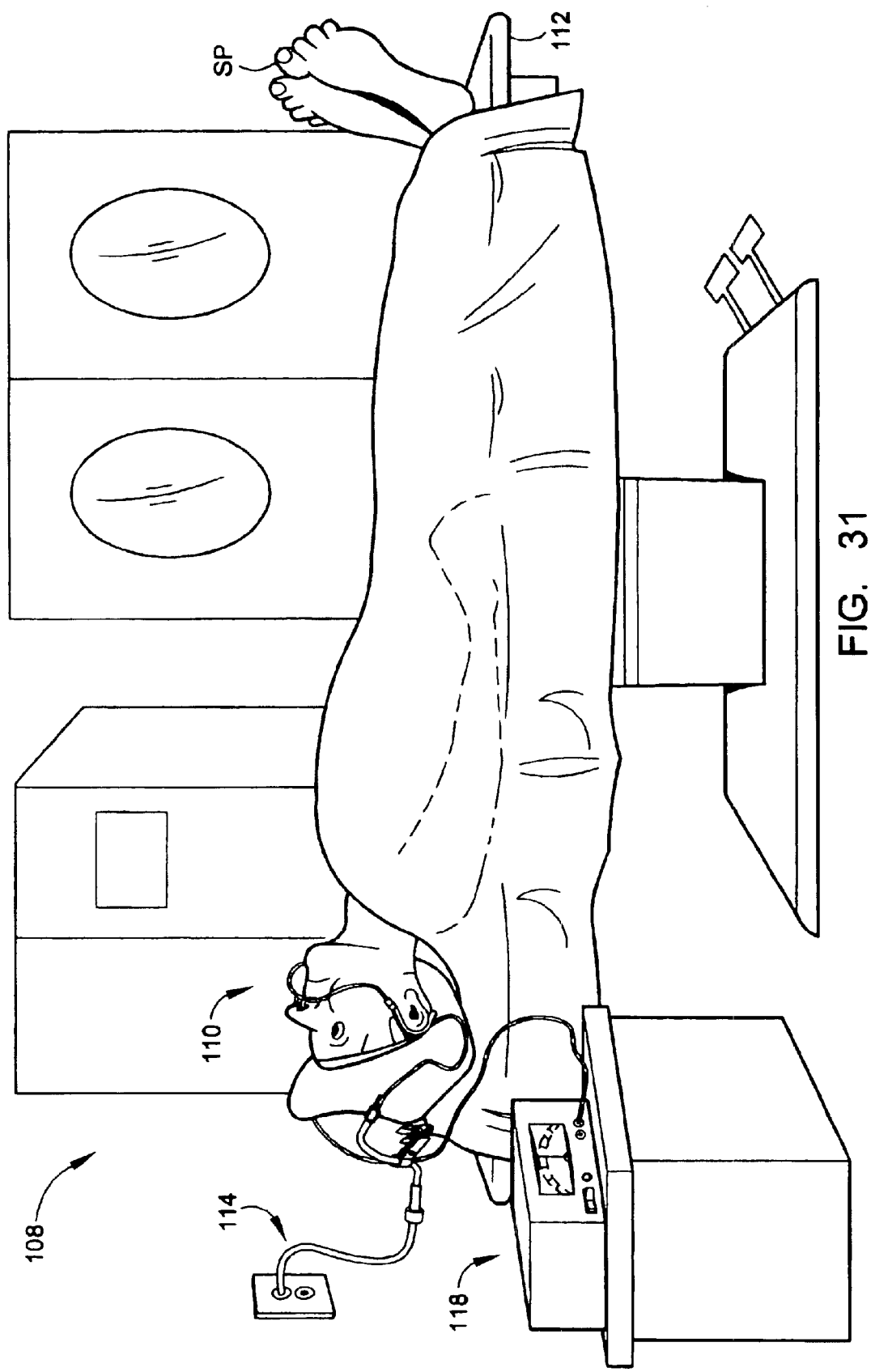
FIG. 31 is a pictorial view of a preferred embodiment of a nasal cannula system, which is constructed in accordance with the present invention.

Referring now to the drawings and more particularly to FIGS. 23–24 and 31, there is illustrated in a preferred embodiment a nasal cannula system 108, which is constructed in accordance with the present invention. The nasal cannula system 108 is illustrated in FIG. 23 being utilized by a surgical patient (SP) who is lying prone on an operating table 112 (FIG. 31) where it is desired to deliver to the patient (SP) a supply 114 of air or oxygen under pressure as well as to collect and analyze exhaled gases emitted from the lungs of the patient (SP) via a gas collection system 118.

Considering now the nasal cannula system 108 in greater detail with reference to FIGS. 23–24 and 31, the nasal cannula system 108 generally comprises a nasal cannula assembly 110, that is coupled between a flexible tube member 120 that facilitate the delivery of oxygen from the oxygen supply 114 and another flexible tube member 160 that facilitates the sampling of exhaled gas exhaled from the lungs of the patient (SP). The flexible tube member 120 is adapted to be coupled to the nasal cannula assembly 110 via a coupler 124, while the flexible tube member 160 is adapted to be coupled to the nasal cannula assembly 110 via another coupler 142. It should be noted that the nasal cannula assembly 110 is universal in nature and may be coupled in a reverse manner to the flexible tube member 120 and 160 respectively.

As best seen in FIGS. 23 and 31, the distal end of the flexible tube member 120, terminates in a coupler 121, and is held within a securing arrangement 122 (FIG. 23) that permits the tube member 120 to be secured to the shirt of the patient P or to a bottom sheet. The securing arrangement 122 is similar to the securing arrangement 22 described earlier and includes a flexible plastic strap 126 and a plastic clip 128. The flexible strap 126 is adapted to be secured in a friction tight fit around the tube member 120 without pinching or closing off the flow of fluids within the tube member 120, and is further adapted to be coupled to the plastic clip 128 for holding the clip 128 in a stationary position relative to the strap 126. From the foregoing it should be understood by those skilled in the art that the securing arrangement 122 is composed on two plastic parts that are coupled together without the use of any metallic parts, which allows the arrangement 122 to be easily and quickly assembled at a relatively low cost. As the securing arrangement 122 is substantially similar to the securing arrangement 22, the securing arrangement 122 will not be described hereinafter in greater detail.

Considering now the nasal cannula assembly 110 in greater detail with reference to FIGS. 23–24, the nasal cannula assembly 110 generally includes a divided or split oxygen/carbon dioxide nasal cannula 132, a pair of adjustment or extension tubes including a gas delivery extension tube 140 and a gas sampling extension tube 150, and a pair 116 of flexible earpiece members 144 and 152 respectively that are adapted to partially hook on the ears of the patient (SP). This is an important feature of the present invention since the earpiece members 144 and 152 are not full ear loops their smooth sharply rounded shapes allow them to secure to top portions of a patient's ears and not completely around them; thus, the earpieces are universal in nature and will easily secure to any ear regardless of size.

As best seen in FIG. 24, the divided or split oxygen/carbon dioxide nasal cannula 132 includes a single delivery/collection tube 134 for both the delivery of oxygen and the collection of gases, such as carbon dioxide. The tube 134 has two upstanding trimmable prongs 136 and 138 that are adapted to be inserted into the nostrils (N) of the patient (SP). Exhale gases are collected from the nasal prong 136 via the gas collection system 118 and oxygen is delivered from the oxygen supply 114 via the nasal prong 138. A septum or partition 154 is present inside the tube 134 and is disposed midway between the nasal prong 136 and the nasal prong 138 in order to separate the delivered oxygen from the exhaled carbon dioxide.

Figure 25:
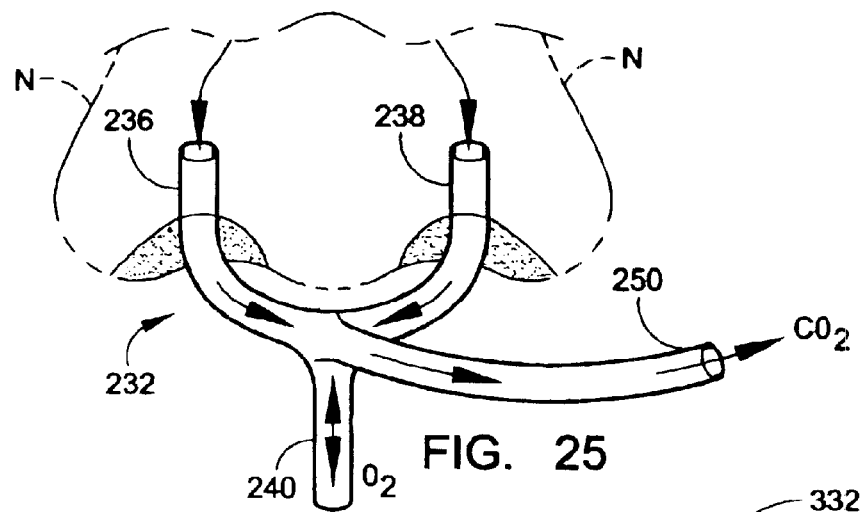
FIG. 25 is a pictorial view of another preferred embodiment of a nasal/oral cannula assembly, which is constructed in accordance with the present invention for a nasal/oral cannula system.

While in the preferred embodiment of the present invention the divided nasal cannula 132 has been described as having a septum or partition 154 to facilitate separating the delivery gases from the exhaled gases, it should be understood by those skilled in the art that other types and kinds of cannula are contemplated. For example, in FIG. 25 there is shown a schematic illustration of a nasal cannula 232 for delivery of oxygen and collection of exhaled gases according to the present invention. The oral/nasal cannula 232 includes a pair of nasal prongs 236 and 238 for insertion into the nostrils N of a patient and a gas delivery prong 240 that is coupled to a gas delivery extension tube (not shown) that is similar to gas delivery extension tube 140. The cannula 232 also has a gas collection tube 250 for collection of the exhaled gases for analysis. The gas collection tube 250 is adapted to be coupled to a gas sampling extension tube (not shown) that is similar to gas sampling extension tube 150. As best seen in FIG. 25, the nasal prongs 236, 238, the gas delivery prong 240 and the gas collection tube 250 meet at a single junction, which is preferably minimized to reduce void volume, thereby reducing mixing of the gases and maintaining the response time.

Figure 26:
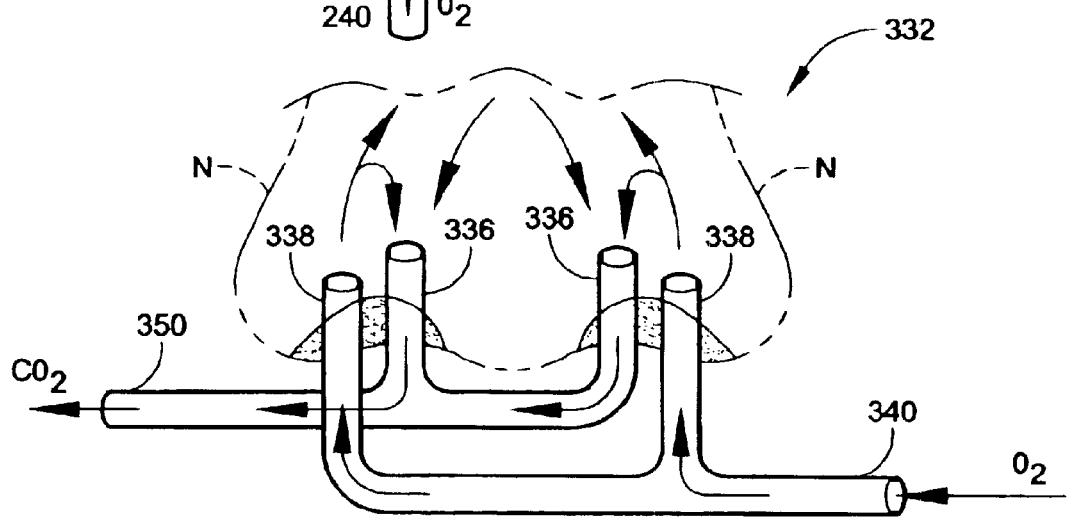
FIG. 26 is a pictorial view of a preferred embodiment of a double nasal oxygen/carbon dioxide cannula assembly, which is constructed in accordance with the present invention for a nasal/oral cannula system.

FIG. 26 illustrates another cannula example, where a double oxygen/carbon dioxide nasal cannula 332 includes a first pair of nasal prongs 336 for insertion into nostrils N of the patient (SP). First nasal prongs 3336 are connected to a first hollow tube 350, which is adapted to be coupled to a gas delivery extension tube (not shown) similar to gas delivery extension tube 140. First hollow tube 350 is substantially perpendicular to first nasal prongs 336. In addition, nasal cannula 332 has a second pair of nasal prongs 338 for insertion into nostrils N. Second nasal prongs 338 are attached to a second hollow tube 340 in a substantially perpendicular orientation. First nasal prongs 338 and first hollow tube 350 are intended for the collection of exhaled gases from the patient, while the second nasal prongs 338 and the second hollow tube 340 are intended to deliver oxygen to the patient, so that nasal cannula 32 is capable of simultaneous oxygen delivery and gas collection.

Figure 27:
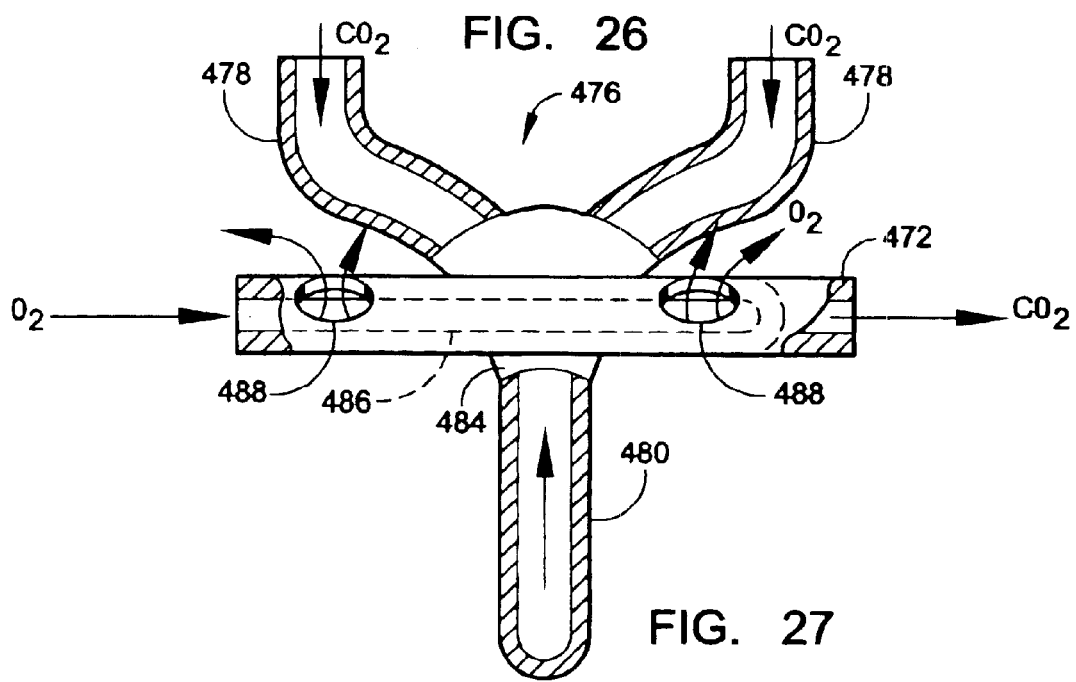
FIG. 27 is a cross sectional view of another preferred embodiment of a nasal/oral cannula assembly, which is constructed in accordance with the present invention for a nasal/oral cannula system.

Another illustrative example is shown in FIG. 27. In this regard, a nasal cannula 476 has a pair of nasal prongs 478 for insertion into the nostrils N of the patient (SP). Cannula 478 further includes an oral prong 480 for placement near the oral cavity of the patient to form an oral/nasal cannula. Cannula 476 also has a gas collection tube 472 for collection of the exhaled gases for analysis. Nasal prongs 478, oral prong 480 and gas collection tube 472 meet at a single junction 484, which is preferably minimized to reduce void volume. Although cannula 476 also features an oxygen tube 486 for lying near the nostrils N of the patient (SP) and more preferably above or below the nostrils N of the patient, substantially parallel with the upper lip of the patient, oxygen is not delivered through a second set of nasal prongs. Instead, oxygen tube 486 has two holes 488, through which oxygen is delivered to the patient. Holes 488 are placed near the nostrils of the patient yet do not enter the nostrils, thereby preventing the delivered oxygen from entering as a forceful stream of gases, which dilutes the exhaled gases and reduces the accuracy of gas analysis.

Figure 28:
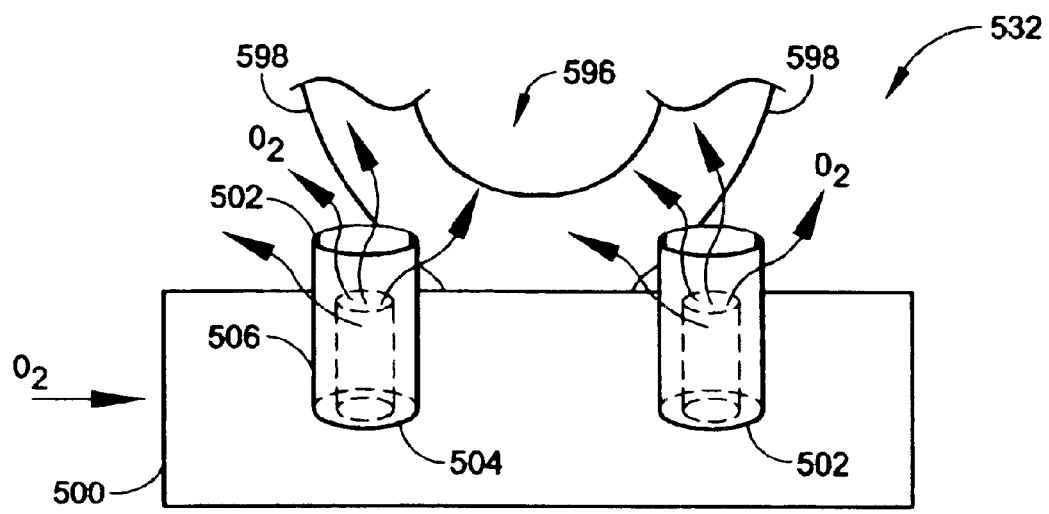
FIG. 28 is a cross sectional view of still yet another preferred embodiment of a nasal/oral cannula assembly, which is constructed in accordance in accordance with the present invention for a nasal/oral cannula system.

FIG. 28 provides a detailed illustration of yet another example of an oral/nasal cannula 596 according to the present invention. FIG. 28 shows a portion of an oral/nasal cannula 596, showing a section of a pair of nasal prongs 598 for receiving exhaled carbon dioxide, an oxygen tube 500 and a pair of second nasal prongs 502. As clearly illustrated, oxygen is delivered through oxygen tube 500 and is then dispersed through second nasal prongs 502. Preferably, the second nasal prongs 502 are constructed from two cylinders, in order to ensure that oxygen is delivered to the nostrils of the patient efficiently, yet is quickly dispersed within the nasal cavity. The first cylinder is an inner cylinder 504, preferably made from a substantially porous hydrophobic material. The material is preferably hydrophobic to prevent absorption of moisture. Inner cylinder 504 is surrounded by an outer cylinder 506, also preferably made from a substantially porous hydrophobic material, such that oxygen is dispersed throughout the nostrils of the patient, rather than entering the nasal cavity as a highly pressurized stream of gas.

Figure 29:
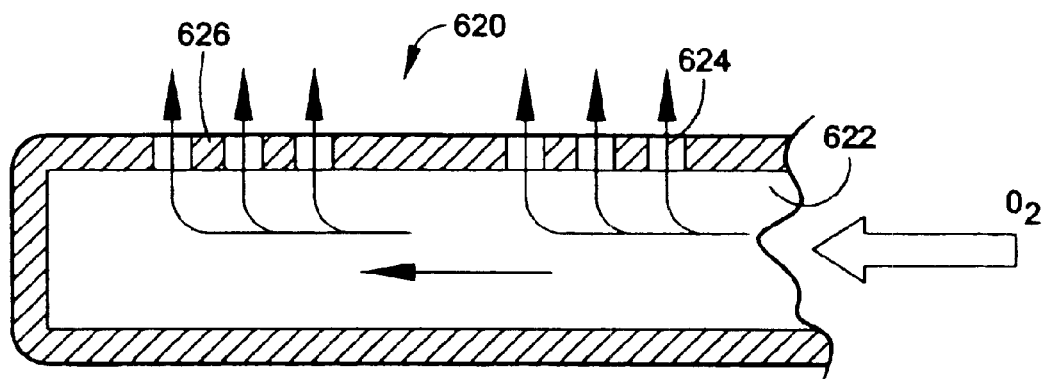
FIGS. 29–30 illustrate a cannula with equal oxygen delivery to each nostril according to the present invention.

FIG. 29 shows a cross-sectional view of the oxygen-delivery portion of yet another exemplary oral/nasal cannula 620 according to the present invention. In this example, cannula 620 has an oxygen delivery tube 622 for delivery oxygen to two sets of outputs 624 and 626. Each set of outputs 624 and 626 includes at least two outputs, although three are shown here for illustrative purposes, without any intention of being limiting. Again, the outputs could be holes, with a porous screen, or nasal prongs as shown previously. The advantage of this configuration is that oxygen is distributed more evenly between both sets of outputs 624 and 626. Such a situation arises because the resistance of both sets of outputs 624 and 626 to the flow of oxygen is much greater than the resistance of the connecting portion of oxygen delivery tube 622.

Figure 30:
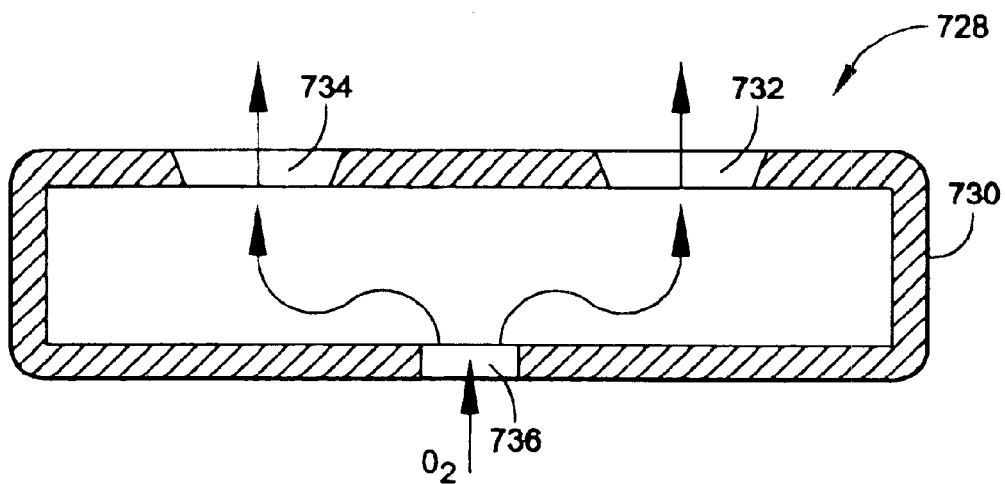

FIG. 30 shows a cross-sectional view of the oxygen-delivery portion of still yet another exemplary oral/nasal cannula 728 according to the present invention. The cannula 728 has an oxygen delivery tube 730 for delivery oxygen to two sets of outputs 732 and 734. Each set of outputs 732 and 734 includes at least one output, although only one is shown here for illustrative purposes, without any intention of being limiting. Again, the outputs could be holes, holes with a porous screen, or nasal prongs as shown previously. Additionally, oxygen delivery tube 730 features a centrally located input 736 for the delivery of oxygen. Preferably, centrally located input 736 is located substantially equidistantly to outputs 732 and 734. The advantage of this configuration is that oxygen is distributed more evenly between both sets of outputs 732 and 734 even for their relatively lower resistance to air flow in comparison to the resistance of oxygen delivery tube 730. Such a situation arises because the resistance of each output 732 and 734 to the flow of oxygen is equal.

In summary then, while in the preferred embodiment of the present invention a divided nasal cannula 132 was described as having a septum or partition 154 to facilitate separating the delivery gases from the exhaled gases, there is no intention of limiting the scope of the present invention to this configuration alone as other configurations are shown and contemplated by the present invention.

Considering now the pair 116 of flexible earpiece members 144 and 152 in greater detail, as the earpiece members 144 and 152 are substantially identical, only earpiece member 144 will be described hereinafter in greater detail.

As best seen in FIG. 23, earpiece member 144 is composed of a soft flexible plastic material with an open recessed channel 146 that terminates at it front end 145 in a protection tip 147 having a tube entrance hole 143, and at its rear end 149, in a locking tube hole 148 that extends from a base portion of the channel 146 to a top lip portion of the channel 146. In this regard, the locking tube hole 148 is generally an oval shaped hole. The shape and orientation of the locking tube hole 148 relative to the distal end of the open recessed channel 146 is an important feature of the present invention as will be explained hereinafter in greater detail. That is, the locking tube hole 148 cooperates with the gas delivery tube 140 in such a manner so that when the gas delivery tube 140 is slightly pulled upward, (near the locking tube hole 148 as best seen in FIG. 23, the tube 140 becomes lodged or locked within the hole 148, thereby greatly reducing, if not completely eliminating tube slippage from the earpiece 144.

As best seen in FIG. 23, the tube 134 is coupled between the gas delivery extension tube 140 and the gas sampling extension tube 150. In this regard, the tube 134 has a greater diameter than the extension tubes 140 and 150 respectively. This is an important feature of the present invention as each individual tube entrance hole, such as the tube entrance hole 143 of earpiece 144, has a sufficiently large diameter to allow the extension tube 140 to pass therethrough but not such a sufficiently large diameter to allow the delivery/collection tube 134 to pass therethrough. In this regard, earpiece 144 acts as a stop preventing the delivery/collection tube from being captured in the earpiece 144.

As best seen in FIG. 23, the tube 134 is coupled at its proximate end to the gas sampling extension tube 150 whose distal end is coupled in an airtight manner to the reduction connector 124. In this manner, a fluid or air path is established between the oxygen source 14 and the nasal cannula assembly 110 when the extension tube 150 is interconnected to the reduction connector 124. In the preferred embodiment of the present invention, the reduction connector 124 has been described as being attached to the flexible tube member 120. It should be understood however, by those skilled in the art, that the reduction connector 124 could be attached to the end of the extension tube 150 as part of the nasal cannula assembly 110.

The extension tube 150 is slidably mounted to the earpiece 152 and cooperates with the earpiece 152 to further facilitate supporting the cannula nosepiece 132. As the earpiece 152 is similar in construction to the earpiece 144, earpiece 152 will not be described hereinafter in greater detail. In a similar nature, as the manner of adjusting the position of the cannula nosepiece 132 relative to the ear piece 152 is substantially similar as the distance adjustment between the earpiece 144 and the cannula nosepiece 132, no further disclosure relative to adjustment is necessary except to mention, that when the extension tube 150 is slightly pulled upward from the recessed channel within the earpiece 152, the tube becomes secured within the earpiece 152 in substantially the same manner as tube 140 becomes secured within the earpiece 144.

Considering now the earpiece 144 in greater detail with reference to FIGS. 23–24, the earpiece 144 is composed of a soft flexible plastic material that is non skin irritating and that is sufficiently ridge to retain its shape so that it will remain lodged between the head and a top back portion of the ear of the patient when worn over extended periods of time. In this regard, the texture and shape of the earpiece 144 permits the earpiece 144 to be worn while supporting the nasal cannula 132 without causing any skin irritation. It should be understood by those skilled in the art, that the earpiece 144 does not completely hook or loop behind the ear of the patient, but instead only rests on the ear in that small space that begins where the top portion of the ear attaches to the head and then extends before dropping sharply downward. The earpiece 144 is also configured to provide the patient with a maximum degree of comfort when wearing the cannula 132 by supporting the cannula 132 from the extension tube 140 along a support angle that extends between the distal end of the cannula 132 and the proximal tip 147 of the earpiece which is disposed in the space between the ear and the head of the patient located at the top front portion of the ear. This support angle is an angle of about 30 degrees, which is a natural angle found in the face and head structure of most people relative to the angle between the base of the nose (where the cannula is disposed) and the front portion of the ear (where the tip 147 of the earpiece 144 is disposed when worn by the patient). To further enhance the comfort of the patient when wearing the earpiece 144, the earpiece 144 is further configured to be worn in the space between the head and a top portion of the ear. In this regard, the earpiece has a width of between about 5 mm and 10 mm to rest comfortably between the head and ear of the patient (SP). A most preferred width is about 7.5 mm, which width allows the earpiece to be worn for extended periods of time without causing any significant skin irritation to the patient (SP).

Considering the earpiece 144 in still greater detail, the earpiece 144 has a unitary construction that extends along it three major sections that include: 1) its front or tube guiding portion 147, which is integrally connected to 2) its central or tube retaining recessed channel portion 146, which is integrally connected to 3) its rear or tube securing portion 149. The three sections form a short generally U-shaped hook that has an overall length that is only sufficient to be disposed in a limited space that extends between the ear and the head at the front of the ear extending rearward to where the ear falls sharply downward.

Considering now the front or tube guiding portion 147 in greater detail, the front or tube guiding portion is identical in construction to the front or tube guide portion 47. That is, the tube guiding portion 147 has a centrally disposed tube guide hole 143 that extends from front to rear along the entire longitudinal length of the tube guide portion 147. The tube guide hole 143 is not round but instead it has a rounded bottom portion and a straight top portion. This is an important feature of the present invention as the tube guide portion 147 not only provides a front bridge that guides the extension tube 140 into the recessed channel portion 146 of the earpiece 144 but the tube guide portion retains the extension tube 140 within the earpiece. The entrance shape and exit shape of the hole 143 also helps to prevent the extension tube 140 from snagging or being crimped, thereby assure the free flow of gases.

Considering now the central portion 146 in greater detail, the central portion has a general U-shape with a radius of about 28 degrees. This radius angle is important as it allows the extension tube 140 to be extended to the cannula 132 at about a 30-degree angle as noted earlier. This U-shape also helps to assure the extension tube is captured within the recessed channel and held for sliding movement.

Considering now the its rear or tube securing portion 149 of the earpiece in greater detail, the rear portion 149 is identical in structure to the rear portion of earpiece 44 and includes a bridge 160, an exit hole 162, an oval shaped tube locking hole 148 and a ramp 164. The locking hole 148, the bridge 160, the exit hole 162, and the ramp 164 cooperate to retain the extension tube 140 within the earpiece 144 as well as to help secure the extension tube 140 within the earpiece 144 so that the extension tube does not crimp nor slip out of the earpiece. It should be understood by those skilled in the art, that the unique structure of the earpiece prevents the extension tube from being accidentally released from it fixed position. This is an important feature of the present invention as the earpieces secure the cannula 132 in a fixed position so there is substantially no migration thereby greatly reducing if not substantially eliminating creating irritation spots on the skin of the patient.

While particular embodiments of the present invention have been disclosed, it is to be understood that various different modifications are possible and are contemplated within the true spirit and scope of the appended claims. For example, the ear piece support tube 40 described as having its distal end plugged with a removable plastic stop 42 could also be crimped or clamped at its distal end to provide an airtight seal preventing fluid from escaping from the distal end of the tube 40. As another example, the securing arrangement 22 is described as being constructed of all plastic parts could also have metal parts. Based on the foregoing, there is no intention, therefore, of limitations to the exact abstract or disclosure herein presented.

I claim:

1. A cannula assembly, comprising:
   slider tube extension means for helping to facilitate a distance adjustment;
   nasal cannula means coupled between said slider tube extension means for facilitating both the delivery of and collection of gases;
   ear piece means coupled to said nasal cannula means by said slider tube extension means for facilitating supporting said nasal cannula means from the ears of a user; and
   said ear piece means including open recessed channel means for helping to facilitate user adjustment of the distance between said nasal cannula means and said ear piece means;
   wherein said ear piece further includes means defining a tube locking hole for helping to secure said nasal cannula means in a fixed position relative to said ear piece means; and
   wherein said ear piece means further includes stop means for helping to limit an adjustment distance between said nasal cannula means and said ear piece means.

2. The cannula assembly according to claim 1, wherein said nasal cannula means is a divided oxygen/carbon dioxide nasal cannula having a pair of spaced apart nasal tips of sufficient length for insertion into the nostrils of the user.

3. The cannula assembly according to claim 2, wherein said pair of spaced apart nasal tips have substantially smaller outer diameter than said nasal delivery tube.

4. The cannula assembly according to claim 3, wherein said pair of spaced apart nasal tips are trimmable to custom fit the user.

5. The cannula assembly according to claim 4, wherein said slider tube extension means includes a pair of extension tubes each having a given diameter.

6. The cannula assembly according to claim 5, wherein said ear piece means includes a pair of ear pieces; and
   wherein each individual one of said pair of ear pieces has disposed thereon an open recessed channel for helping to facilitate supporting therein at least a portion of an individual one of said pair of extension tubes.

7. The cannula assembly according to claim 5, wherein stop means is coupled to a proximal end of said ear piece means and includes means defining a tube entrance hole for helping to facilitate guiding an individual one of said pair of extension tubes into a corresponding one of said open recessed channel and to facilitate securing slidingly an individual one of said pair of extension tubes to said ear piece.

8. The cannula assembly according to claim 7, further comprising:
   a securing clip mounted to said section of fluid delivery tubing to help secure the fluid delivery tubing in a fixed position relative to the user.

9. The cannula assembly according to claim 8, further comprising:
   a securing clip mounted to the other one of said pair of extension tubes to help secure the other one of said pair of extension tubes in a fixed position relative to the user.

10. A cannula system, comprising:
    a nasal cannula coupled to a pair of extension tubes;
    a pair of earpieces for supporting and retaining said extension tubes and said nasal cannula in a fixed position; and
    wherein each individual earpiece includes a pair of guides with a recessed channel disposed therebetween for receiving and retaining therein an individual one of the extension tubes;
    wherein one of said pair of guides is an exit bridge disposed adjacent to an exit hole, said exit bridge having a hole extending therethrough for providing access to said exit hole to provide an extension tube exit path from said recessed channel to said exit hole;
    wherein said recessed channel terminates in an inclined ramp disposed at about said oval shaped exit hole;
    wherein said exit hole is oval shape having its long axis extending along the longitudinal axis of said earpiece;
    wherein said inclined ramp reaches its apex at the distal end of the long axis of said oval exit hole to provide an exit path that causes the extension tube to be wedged into engagement with said exit bridge;
    wherein the other one of said bridges is an entrance bridge, said entrance bridge having an entrance hole extending therethrough for providing access to said recessed channel to provide an extension tube entrance path from said nasal cannula to said recessed channel;
    wherein said entrance bridge, said inclined ramp and said exit bridge cooperate to facilitate capturing the extension tube in a fixed position to secure said cannula at a desired position relative to the nostrils of a patient;
    wherein said nasal cannula has a single tube with at least one gas outlet channel and with at least one gas inlet channel for facilitating both the delivery of and the collection of gases;
    said single tube having a given diameter and being disposed between the pair of extension tubes, wherein each extension tube has another given diameter substantially smaller than said given diameter; and
    wherein each ear piece has a tube entrance hole with a sufficient diameter for receiving therethrough one of said pair of extension tubes but not a sufficient diameter for receiving therethrough said single tube for helping to limit an adjustment distance between the nasal cannula and individual ones of said pair of ear pieces.

11. A cannula assembly, comprising:

a nasal cannula having a centrally disposed plug wherein on one side of said plug said cannula includes at least one gas outlet channel and wherein on another side of said plug said cannula includes at least one gas inlet channel;

a pair of extension tubes, wherein one of said pair of extension tubes is coupled to said at least one gas outlet channel and wherein another one of said pair of extension tubes is coupled to said at least one gas inlet channel; and a pair of ear pieces, at least one of said pair of ear pieces having stop means for helping to limit an adjustment distance between said nasal cannula and the ear piece.

12. A cannula assembly according to claim 11, wherein each ear piece further having a tube locking hole disposed at a distal end of an open recessed channel disposed in a top portion of the ear piece, said open recessed channel being in alignment with tube entrance hole for receiving slidingly therein an individual one of said pair of extension tubes to facilitate supporting from the ear piece said nasal cannula and to further help facilitate adjusting the distance between the nasal cannula and individual ones of said pair of ear pieces to position said nasal cannula in proper position relative to the nostrils of a user.

13. A cannula assembly according to claim 11, wherein each ear piece further includes means defining a tube locking hole for helping to secure said nasal cannula in a fixed position relative to said ear piece.

14. The cannula system according to claim 11, wherein said nasal cannula is a divided nasal cannula for facilitating the delivery of and collection of gases.

15. A cannula assembly, comprising:

a nasal cannula having a centrally disposed plug wherein on one side of said plug said cannula includes at least one gas outlet channel and wherein on another side of said cannula includes at least one gas inlet channel;

a pair of extension tubes, wherein one of said pair of extension tubes is coupled to said at least one gas outlet chanel and wherein another one of said pair of extension tubes is coupled to said at least one gas inlet channel;

a pair of ear pieces, each ear piece having a pair of guides with a recessed channel disposed therebetween for receiving and retaining therein an individual one of the extension tubes; and wherein one of said pair of guides is an exit bridge disposed adjacent to an exit hole, said exit bridge and said hole cooperating to retain said extension tube within the ear piece and to help prevent said extension tube from being accidentally released from a fixed position relative to the ear piece.

16. The cannula system according to claim 15, wherein each ear piece further having stop means for helping to limit an adjustment distance between said nasal cannula and the ear piece.

17. The cannula system according to claim 15, wherein said recessed channel terminates at its distal end in an inclined ramp disposed at about said exit hole.

18. The cannula system according to claim 17, wherein said exit hole is oval shape having its long axis extending along the longitudinal axis of said earpiece.

19. The cannula system according to claim 18, wherein said inclined ramp reaches it apex at the distal end of the long axis of said oval said hole to provide an exit path that cause the extension tube to be wedged into engagement with said exit bridge.

20. The cannula system according to claim 19, wherein the other one of said bridges is an entrance bridge, said entrance bridge having an entrance hole extending therethrough for providing access to said recessed channel to provide an extension tube entrance path from said nasal cannula to said recessed channel; and wherein said entrance bridge, said inclined ramp and said exit bridge cooperate to facilitate capturing the extension tube in a fixed position to secure said cannula at a desired position relative to the nostrils of a patient.

* * * * *